US00PP11201P

United States Patent [19]

Crist

[11] Patent Number: Plant 11,201

[45] Date of Patent: Feb. 1, 2000

[54] APPLE TREE DESIGNATED 'CB515'

[75] Inventor: Jeffrey D. Crist, Walden, N.Y.

[73] Assignee: Adams County Nursery, Inc., Aspers, Pa.

[21] Appl. No.: 09/079,297

[22] Filed: May 13, 1998

[51] Int. Cl.[7] ..... A01H 5/00

[52] U.S. Cl. ..... Plt./170

[58] Field of Search ..... Plt./161, 170

[56] References Cited

U.S. PATENT DOCUMENTS

P.P. 7,820 3/1992 Teeple et al. ..... Plt./170

P.P. 8,010 10/1992 Thome ..... Plt./170

*Primary Examiner*—Howard J. Locker
*Assistant Examiner*—Wendy A Baker
*Attorney, Agent, or Firm*—James A. Lucas; Driggs, Lucas, Brubaker & Hogg Co., L.P.A.

[57] ABSTRACT

A new and distinct strain of apple, designated 'CB515', originated as a limb sport on an 'Empire' tree. It matures with 'Empire' or slightly earlier and develops red color 2½ weeks earlier than the parent. Other significant improvements over 'Empire' include increased color intensity, a higher percentage of red color and increased spur density and cropping.

3 Drawing Sheets

BACKGROUND OF THE DISCLOSURE

This invention relates to Apple Trees and, more specifically, to apple trees referred to as a variety, or budsport, of *Malus domestica Borkh*. 'Empire'.

I discovered this new and unique variety of apple tree as a limb sport on an 'Empire' in a cultivated area near Walden, N.Y. The tree of this invention produces a fruit of attractive commercial value, coloring 2½ weeks before 'Empire'.

This new variety of apple was asexually reproduced by grafting near Walden, N.Y., and Aspers, Pa., and such reproduction has shown this new variety to come true in three successive generations. This propagation of the new variety by grafting under standard controlled conditions clearly discloses the continued maintenance of the characteristics described herein which distinguish this new variety from the parent cultivar.

SUMMARY OF THE INVENTION

This new and distinctive variety of apple tree produces a fruit with a solid red blush and an attractive finish. The red color is 99%, compared to 60 to 70% on 'Empire'. Color intensity also is superior to 'Empire'.

DESCRIPTION OF THE DRAWINGS

This new variety of apple tree is illustrated by the accompanying photographic drawings, depicting the plant by the best possible color representation using color photography.

BOTANICAL DESCRIPTION OF THE PLANT

Figure 1:
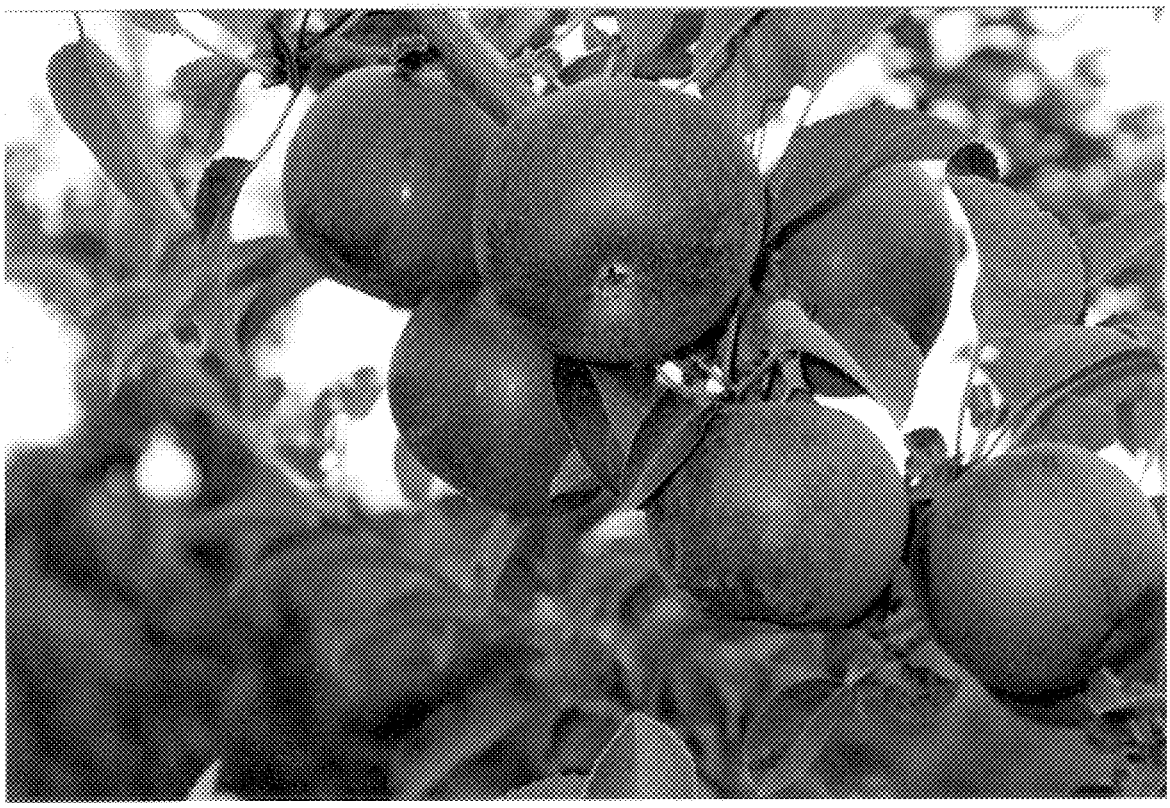
FIG. 1: Close-up of 6 specimens of fruit on the new tree in different orientations to reflect the uniform size, shape and characteristic color and bloom. Also shown is the open calyx with persistent segments.
Figure 2:
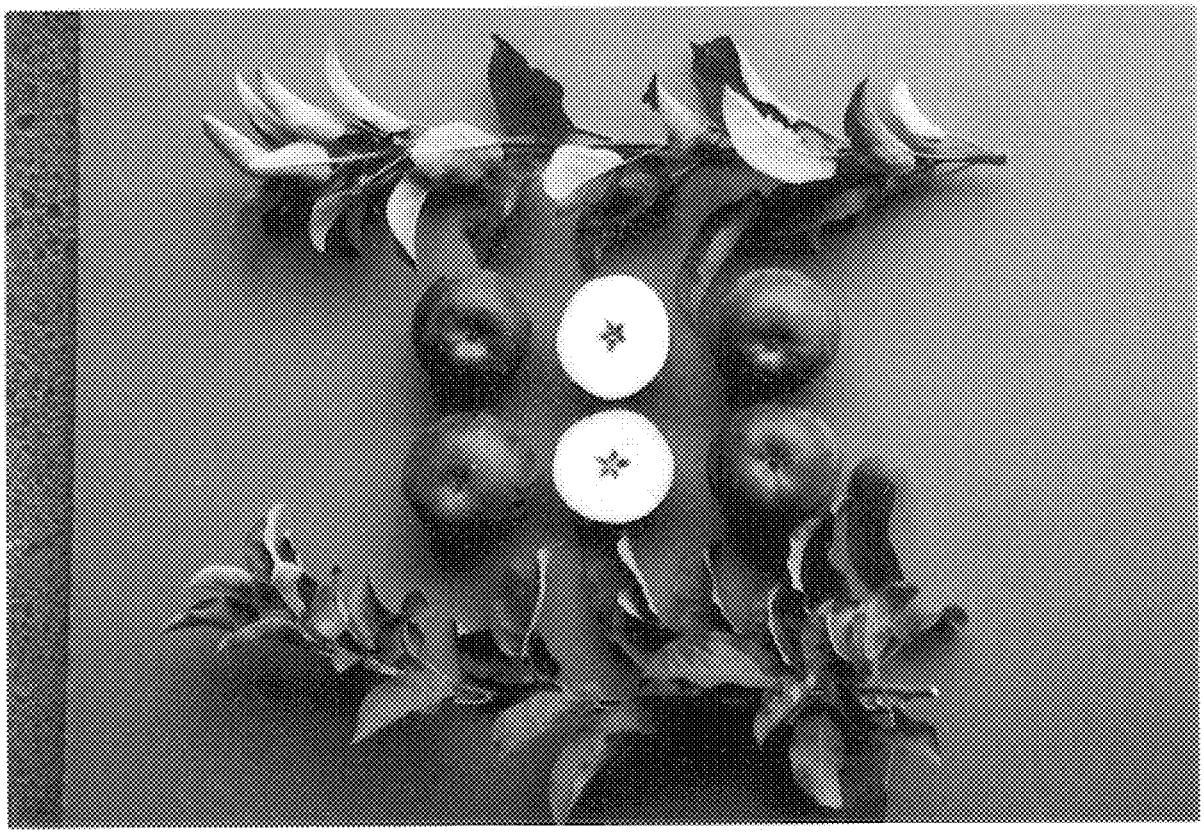
FIG. 2: At center, 4 whole specimens of fruit shown from the calyx end, and 2 partially dissected specimens showing seed cavity and flesh color. At either side of fruit, terminal shoots from a 6-year-old tree, showing current season's growth, leaves, leaf arrangement and leaf spacing.
Figure 3:
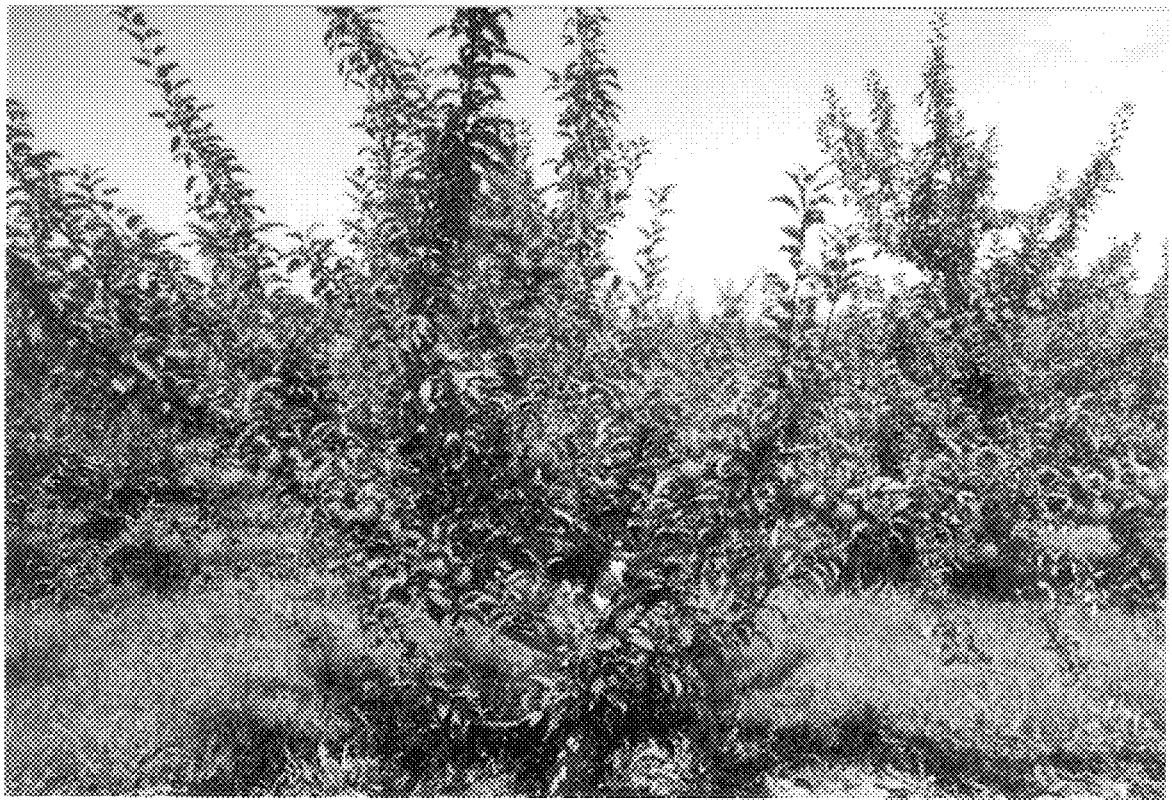
FIG. 3: Second generation, 6-year-old tree, showing canopy form and fruit density.

All color references below are measured against The Royal Horticultural Society Colour Chart. Colors are approximate as color depends on horticultural practices such as light level and fertilization rate, among others.

Parentage: Limb sport on an 'Empire' tree; asexually reproduced by bud grafting.

Tree: 12 ft tall by 10 ft wide and 2 to 3 bushels per tree, on 'M.7' rootstock, at 6 years age, near Walden, NY. Small, compact, greater spur density than 'Empire' (unpatented) or 'Teeple Red Empire' (U.S. Plant Pat. No. 7,820), not as weak as 'TF808' (U.S. Plant Pat. No. 8,010), spreading, open, slow growing, hardy, very productive, regular bearer. Better annual cropper than 'Empire'.

*Trunk.*—Medium girth, smooth; bark color R.H.S. 165B.

*Branches.*—Medium thick, smooth, little branching, brown; Crotch angles for bearing branches average 70° from the vertical, more horizontal than branches of 'Empire' and 'Teeple Red Empire' which average 60° from the vertical.

*Lenticels.*—Numerous, medium.

*Leaves.*—Length — 2¾ inches. Width — 2 inches. Small, medium width, short length, ovate, taper-pointed, medium thick, dark green, R.H.S. 138B (upper surface) and R.H.S. 138C (lower surface).

*Margins.*—Coarsely serrate.

*Petioles.*—Length 1⅜ inches, long, medium thick.

*Flowers.*—Date of first bloom — Apr. 20. Date of full blossom — Apr. 25, in Walden, N.Y. Early, and medium in size and white in color. Fragrance — Mild. Petals — 5 in number; white (R.H.S. 155A) with some pink stripes. Sepals — 5. Stamens — 20. Styles — 5. Pollination — Diploid, self-unfruitful. Compatible pollinizers include early blooming diploid varieties such as 'Liberty', 'Jonamae' and 'Braeburn'.

*Fruit.*—Maturity when described — Hard. Date — Sep. 28, 1997 (matures with or 1 to 3 days earlier than 'Empire'). Size — Uniform. 2¾ inches in diameter, and 2 inches in length Form — Uniform, regular, oblate, less pointed than TF808. Cavity — Symmetrical, flaring, depth ¼ inch, breadth ⅝ inch, no markings. Stem — Medium, pubescent, length ⅝ inch, 0 to 2 bracts. Basin — Length ¼ inch; diameter 13/16 inch; no protrusions. Calyx — Open, segments persistent, obtuse, diameter ¼ inch. Skin — Thin, tender, smooth, glossy. Dots — Obscure, many, circular, white or pink, scattered over most of surface, increasing numbers toward basin. Ground color — Yellow-green, R.H.S. 154D. Color markings — Splashed, blushed, bright red-purple, R.H.S. 59A (as contrasted to striped 'Empire' and 'Teeple Red Empire'). Bloom — Abundant. Scarskin — Wanting. General color effect — Solid red-purple (99%), R.H.S. 59A. Brighter than 'Empire' (grayish-purple R.H.C. 184C). Flesh — Juicy, white with yellow-green tint (R.H.S. 155B). Texture — Firm-soft, fine, crisp. Flavor — Acid. Aroma — Mild. Eating quality — Best, about 13% soluble solids, about 15 lbs. firmness at harvest maturity. Core position — Median (at center of fruit). Bundle area — Medium, elliptical, sometimes irregular. Halves of area — Unequal. Bundles — Green, one whorl. Core lines — Meeting, indistinct in cross-section. Carpellary area — Distinct. Calyx tube — Glabrous, narrow. Depth of tube to shoulder — ½ inch. Seed cells — Mostly open. Cell walls — Thin, Length ⅜ inch, breadth ⅛ inch, broadly ovate in longitudinal section, narrow to medium in cross-section, surface smooth. Seeds — Number perfect 10, largest number in one cell 2, length ⅜ inch. breadth 3/16 inch form acute. Color — Brown.

*Uses.*—Local, dessert markets.

*Keeping quality.*—Good, 120 days in regular atmosphere storage.

*Resistance to insects.*—Medium.

*Resistance to diseases.*—Medium, susceptibility to apple scab similar to 'Empire'.

I claim:

1. A new and distinct variety of Apple Tree, as illustrated and described, characterized by early coloring fruit of full, blushed red color and smooth, glossy finish.

* * * * *